United States Patent [19]

Kowalski

[11] 4,145,614

[45] Mar. 20, 1979

[54] DEVICE FOR PRODUCING TWO- AND/OR THREE-DIMENSIONAL IMAGES OF THREE DIMENSIONAL OBJECTS

[75] Inventor: Günter Kowalski, Hamburg, Fed. Rep. of Germany

[73] Assignee: U.S. Philips Corporation, New York, N.Y.

[21] Appl. No.: 839,619

[22] Filed: Oct. 5, 1977

[30] Foreign Application Priority Data

Oct. 13, 1976 [DE] Fed. Rep. of Germany ....... 2646118

[51] Int. Cl.² .............................................. A61B 6/02
[52] U.S. Cl. ................................ 250/445 T; 250/314
[58] Field of Search ................... 250/445 T, 312, 313, 250/314

[56] References Cited

PUBLICATIONS

Klotz et al., "X-ray 3-D coded aperture imaging: displaying the heart", *Applied Optics,* Aug. 1976, vol. 15, No. 8, pp. 1913–1918.

*Primary Examiner*—Alfred E. Smith
*Assistant Examiner*—T. N. Grigsby
*Attorney, Agent, or Firm*—Thomas A. Briody; Jack E. Haken

[57] ABSTRACT

A device for producing two- and/or three-dimensional images of three-dimensional objects, comprises at least two radiation sources, a detector arrangement, a computer, a processor and a display device, in which a number of radiation sources are arranged on a straight line, the detector device consists of a plurality of detector elements arranged in a plane parallel to the straight line, and means are present to process the signals which can be derived from the detector elements and to supply them to the computer.

3 Claims, 5 Drawing Figures

DEVICE FOR PRODUCING TWO- AND/OR THREE-DIMENSIONAL IMAGES OF THREE DIMENSIONAL OBJECTS

The invention relates to a device for producing two- and/or three-dimensional images of three-dimensional objects, comprising at least two radiation sources, a detector arrangement, a computer, a processor and a display device.

Such devices are known, for example, from "British Journal of Radiology", 1973, pp. 1016–1022, and "Proceedings Nat. Acad. Sci", USA, Vol. 68, September 1971, pp. 2236–2249.

These known devices, so-called X-ray scanners permit of displaying one or at most two adjacent layers of a three-dimensional object, for example of a human body.

A disadvantage is that for displaying a single layer mechanical movements are necessary and that a three-dimensional object can be separated into a set of many layers only stepwise by repeating the scanning process. In the case of moving objects (for example of the beating heart) this results in considerable difficulties, since every scanning operation finds the object in a different orientation.

It is therefore the object of the present invention to provide a device of the kind mentioned in the preamble by means of which images of moving objects can be produced without errors which result from changes in the shape and/or the position of the object.

According to the invention this is achieved in that a number of radiation sources are arranged on a straight line, that the detector device consists of a plurality of detector elements arranged in a plane parallel to the straight line, and that means are present to process the signals which can be derived from the detector elements and to supply them to the computer.

The radiation sources may be switched-on either successively for a short time or simultaneously, in which case the individual rays are modulated differently so as to distinguish them in the further processing.

During the switching-on time of one or of all radiation sources, all detector elements are scanned and their analog output signals are converted into digital values. These digital values are then supplied to the computer, if desired after intermediate storage in a buffer, and processed further in the known manner.

The detector elements may either be read simultaneously or successively. Although a simultaneous reading reduces the evaluation time, each detector element requires its own analog-to-digital converter. In the case of a sequential scanning, a multiplexing device is necessary which supplies the signals in the correct sequence to the analog-to-digital converter and subsequently composes them before supplying them to the computer.

An embodiment of the invention will now be described in greater detail with reference to the drawing.

In the drawing

Figure 3A:
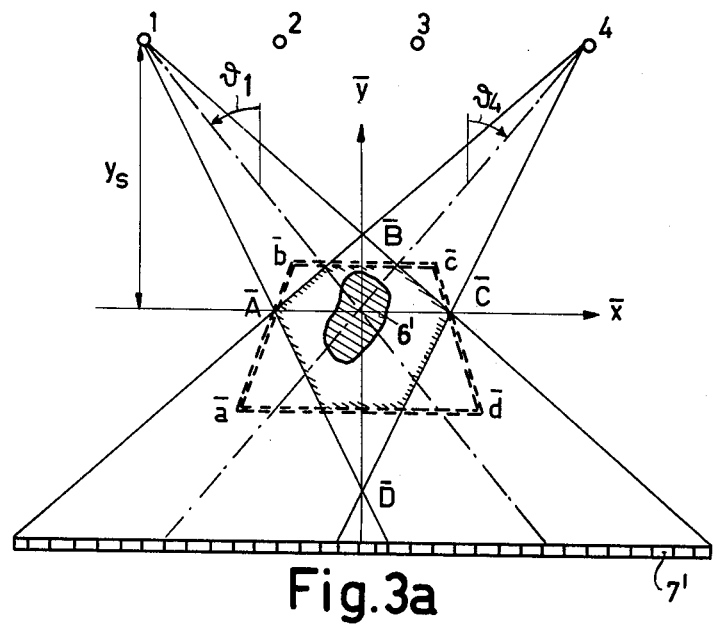

FIGS. 3a, b show the geometrical proportions in the proposed arrangement, and

Figure 1:
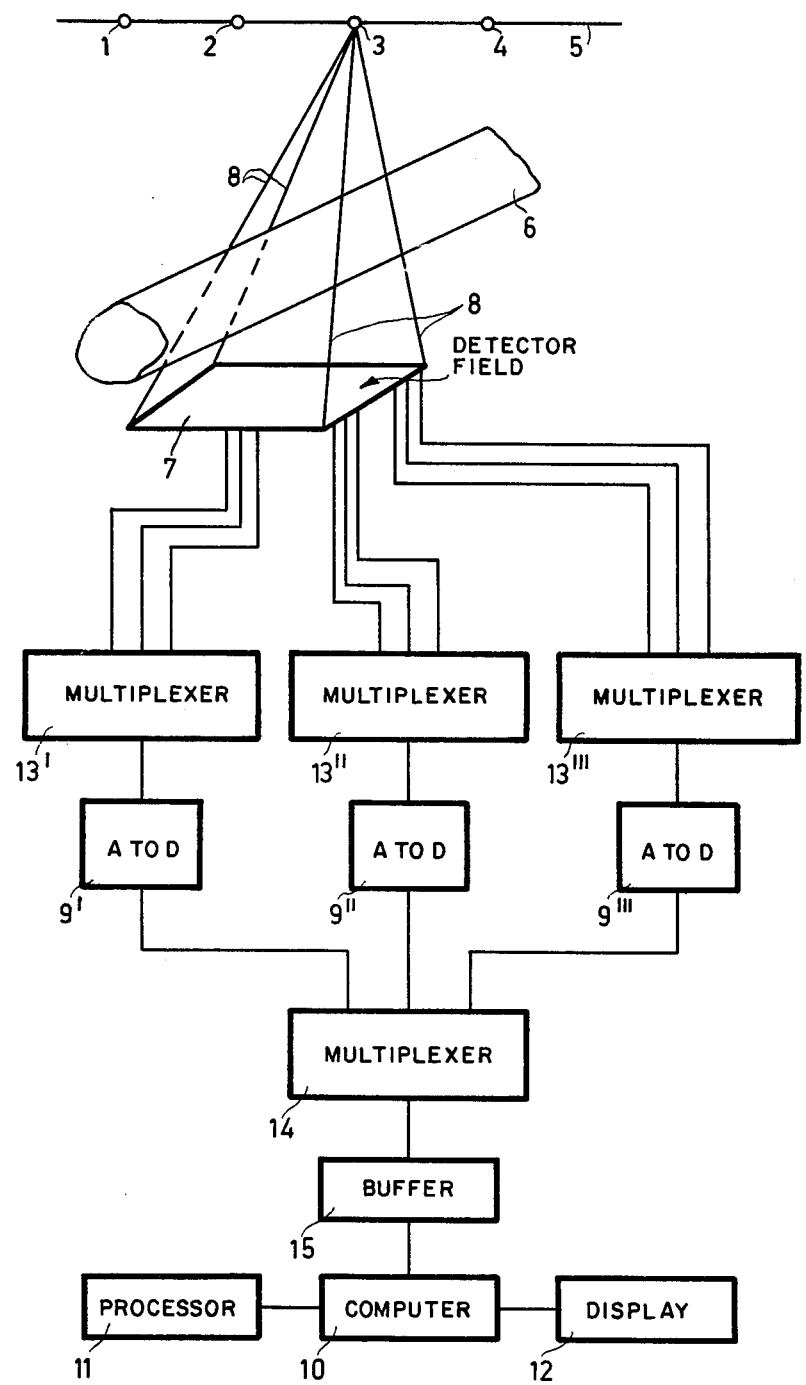
FIG. 1 shows the principle construction of the proposed device.
Figure 4:
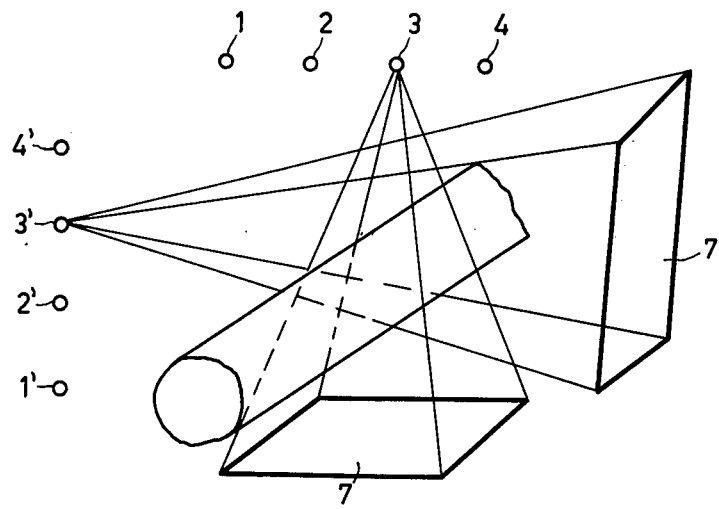

FIG. 4 shows a modified embodiment of the arrangement shown in FIG. 1.

A number of radiation sources (for example X-ray tubes) 1, 2, 3, 4 are arranged on a straight line 5. An object 6 to be examined is present below said radiation sources and below said object a two-dimensional flat detector field 7 is present. Said field is arranged so as to be parallel to the straight line 5.

The rays 8 emanating, for example, from the radiation source 3 penetrate through the object 6 and impinge upon the detector field 7.

Figure 2:
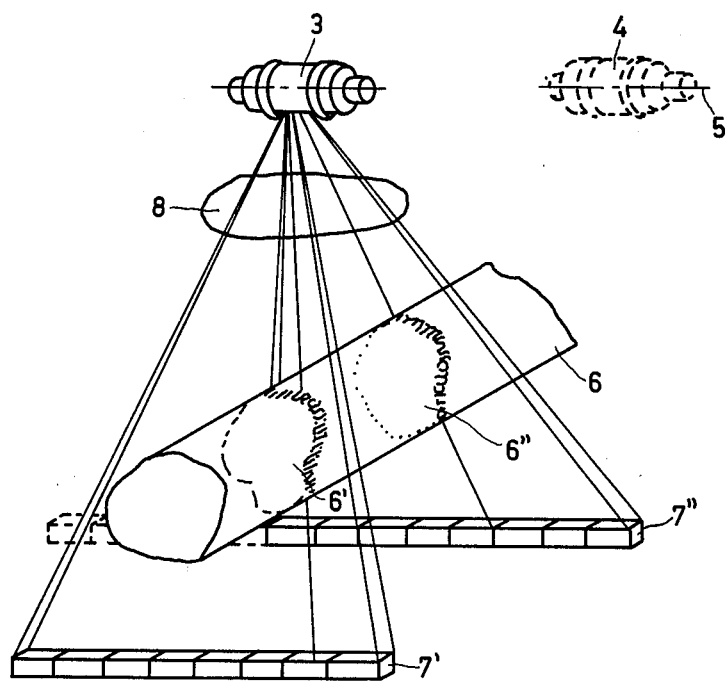
FIG. 2 shows an extended detail drawing.

Said detector field 7 comprises a number of rows with individual detector elements. FIG. 2 shows two of such rows with detector elements 7' and 7". Either linear logarithmic amplifiers may also be associated with said detector elements in known manner.

The detector elements are connected groupwise to the inputs of a first multiplexing device 13', 13", 13''' which, during or after the exposure time, scans all detector element successively and supplies their output signals to an analog-to-digital converter 9. Several outputs of the analog-to-digital converter 9 are again combined to form one channel by means of a second digital multiplexing device 14. These digital signals are then supplied in known manner to a computer 10 and displayed as an image by a display device 12 after processing by means of a processor 11. In accordance with the construction of the device, either the first multiplexing device may be omitted, in the case in which many analog-to-digital converters are present, or the second multiplexing device may be omitted, in the case in which only one analog-to-digital converter is present or the computer 10 has several data input channels. In case the computer 10 cannot take the data with a sufficient velocity, it must be preceded by a buffer memory 15.

It will be explained with reference to FIG. 2 how the problem of the three-dimensional reconstruction is converted into a set of two-dimensional reconstructions. For simplicity, FIG. 2 shows only two radiation sources, namely 3 and 4. Assuming the radiation source 3 to move linearly to the radiation source 4, it is easy to see that all radiation paths between the radiation source and a detector line always traverse only one single slice of the object 6, namely the slices 6' and 6", respectively. In the invention, this assumed movement of the radiation source 3 is replaced by the next radiation source 4. It is advantageous that the mathematical problem is reduced such that the layer 6' is reconstructed only with the measured data of the line 7', since elements of this layer are not associated with any other detector line.

It will be explained briefly how the said reconstruction may be carried out. Of course, other methods are also possible. FIGS. 3a and 3b again show a part of FIG. 2. Shows are the field of ray of the radiation source 1 which radiates at an angle $\theta_1$, as well as the radiation source 4 having a radiation angle $\theta_4$.

Figure 3B:
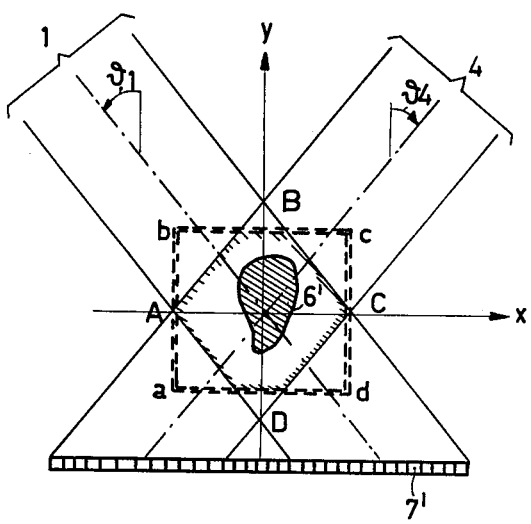

A system of coordinates is described by $\bar{x}, \bar{y}$. A slice 6' of the object 6 may not leave the area $\overline{A}\ \overline{B}\ \overline{C}\ \overline{D}$ in order that it always be entirely in the path of rays. By a simple transformation of coordinates corresponding to $$x = \bar{x} \frac{1}{1 - \bar{y}/y_s} \quad y = \bar{y} \frac{1}{1 - \bar{y}/y_s}$$

the geometry of FIG. 3a is displayed in the geometry of FIG. 3b. The radiation sources 1, 2, 3, 4 apparently disappear into infinity and the reconstruction is limited to a reconstruction of parallel rays. The further steps of the reconstruction are as follows.

1. All projections of the sources are represented by a Fourier series (after the analog-to-digital and logarithmic conversion.
2. The coefficients of the Fourier series are multiplied with a matrix.
3. The result provides the solution coefficients for orthogonal functions of the orthogonal ranges a b c d which describe the object.
4. The object thus reconstructed is displayed geometrically on the geometry $\bar{x}, \bar{y}$. The orthogonal range is then given by $\bar{a}\ \bar{b}\ \bar{c}\ \bar{d}$.

A variation of the invention may consist in two units of the described device arranged so as to be shifted by a larger angle (for example 90°), as shown in FIG. 4. Two or several reconstructions of the object fully separated from each other are carried out and the results are superimposed. In this manner the source range from which the object is irradiated can be expanded. For that purpose, FIG. 4 shows further radiation sources 1', 2', 3', 4' which are shifted with respect to the radiation sources 1, 2, 3, 4 shows in FIG. 1 by 90°.

The radiation sources may be made operative successively. However, in order to reduce the peak load of each radiation source, it is also possible to make all radiation sources operative simultaneously, but to modulate their rays with different frequencies, which may be done mechanically or electrically. The output of each detector may subsequently be separated into many channels by a group of band filters which are tuned to the different modulation frequencies. The signal of each channel is then determined only by the radiation of the associated source.

What is claimed is:

1. A device for producing two- and/or three-dimensional images of three-dimensional objects, comprising at least two radiation sources, a detector array, a computer, a processor and a display device, wherein a number of radiation sources are arranged on a straight line, the detector array includes a plurality of detector elements arranged in a plane parallel to the straight line, and further comprising means for processing signals derived from the detector elements and to supply them to the computer.

2. A device as claimed in claim 1, further comprising means for sequentially actuating the radiation sources and means for scanning the detector elements during the operation times of the radiation sources.

3. A device as claimed in claim 1, further comprising means for the simultaneously actuating the radiation sources, means for the modulating rays emanating from the radiation sources, and means associated with each detector element for processing the signals which are derived from the detector element.

* * * * *